US009814271B2

(12) United States Patent
Goggin et al.

(10) Patent No.: US 9,814,271 B2
(45) Date of Patent: Nov. 14, 2017

(54) MULTIPLE CHAMBER VAPORIZER

(71) Applicants: Haiden Goggin, Pawtucket, RI (US); Daniel Kim, Scarsdale, NY (US)

(72) Inventors: Haiden Goggin, Pawtucket, RI (US); Daniel Kim, Scarsdale, NY (US)

( * ) Notice: Subject to any disclaimer, the term of this patent is extended or adjusted under 35 U.S.C. 154(b) by 136 days.

(21) Appl. No.: 14/994,996

(22) Filed: Jan. 13, 2016

(65) Prior Publication Data

US 2016/0198771 A1 Jul. 14, 2016

Related U.S. Application Data

(60) Provisional application No. 62/102,592, filed on Jan. 13, 2015.

(51) Int. Cl.

| | |
|---|---|
| ***A24F 47/00*** | (2006.01) |
| ***A61M 11/00*** | (2006.01) |
| ***A61M 15/00*** | (2006.01) |
| ***H05B 1/02*** | (2006.01) |
| ***H05B 3/04*** | (2006.01) |
| ***H05B 3/14*** | (2006.01) |
| ***H05B 3/44*** | (2006.01) |

(52) U.S. Cl.
CPC ......... *A24F 47/008* (2013.01); *H05B 1/0252* (2013.01); *H05B 3/04* (2013.01); *H05B 3/141* (2013.01); *H05B 3/146* (2013.01); *H05B 3/44* (2013.01); *H05B 2203/013* (2013.01); *H05B 2203/021* (2013.01); *H05B 2203/022* (2013.01); *H05B 2203/037* (2013.01)

(58) Field of Classification Search
CPC ........ A61M 11/00–11/08; A61M 15/00–15/06
See application file for complete search history.

(56) References Cited

U.S. PATENT DOCUMENTS

| | | | | | |
|---|---|---|---|---|---|
| 9,022,026 | B2 * | 5/2015 | Fang | A24F 47/008 128/202.21 |
| 9,204,670 | B2 * | 12/2015 | Liu | A24F 47/008 |
| 9,259,035 | B2 * | 2/2016 | Terry | A24F 47/008 |
| 9,271,527 | B2 * | 3/2016 | Liu | A24F 47/002 |
| 9,549,573 | B2 * | 1/2017 | Monsees | H05B 3/04 |
| 9,591,876 | B2 * | 3/2017 | Alima | A24F 47/008 |
| 2008/0092912 | A1 * | 4/2008 | Robinson | A24F 47/008 131/200 |
| 2011/0126848 | A1 * | 6/2011 | Zuber | A24F 47/008 131/329 |
| 2014/0000638 | A1 * | 1/2014 | Sebastian | A24F 47/008 131/328 |
| 2014/0060556 | A1 * | 3/2014 | Liu | A24F 47/008 131/329 |
| 2016/0048266 | A1 * | 2/2016 | Smith | G06F 3/0418 345/174 |
| 2016/0089508 | A1 * | 3/2016 | Smith | A61M 15/06 128/200.16 |
| 2016/0325055 | A1 * | 11/2016 | Cameron | A61M 11/005 |

* cited by examiner

*Primary Examiner* — Xuong Chung Trans

(57) ABSTRACT

The present device has at least two chambers for receiving vaporizable components, two heating elements, and circuitry to control heater behavior.

20 Claims, 7 Drawing Sheets

MULTIPLE CHAMBER VAPORIZER

PRIORITY CLAIM

This application claims priority to U.S. Provisional Application Ser. No. 62/102,592, filed Jan. 13, 2015. The above referenced application is incorporated herein by reference as if restated in full.

BACKGROUND

While cannabis has a long history of recreational use, much of the underlying drug delivery technology was in a primitive state because of the illegality of cannabis use. Due to recent medical marijuana reform, patients of painful and terminal illnesses are now able to include cannabis in their pain management treatment. Vaporizers provide an effective means of delivering the medically useful ingredients in cannabis while reducing some of the side effects of earlier delivery methods. However, there remains much room for improvement.

Presently, medical cannabis patients must choose between cannabis concentrates and and cannabis flowers in a given medication dosage. This is at least in part because cannabis concentrate and cannabis flowers require different physical heating structures for proper vaporization. Also, each is best heated using carefully tailored heat profiles.

It is desirable for patients to be able to inhale both flower and concentrate in order to overcome tolerance built up against each individually. Combining flower and concentrate dosages tends to increase the duration and strength of the drug intake. Also, the ability to mix and match diverse flowers and concentrates provides a wide variety of new psychoactive and medicinal effects.

This led to patients requiring multiple vaporizers. However, this is an imperfect solution because it requires additional purchases and additional preparation prior to dosage.

SUMMARY

In one embodiment, the device comprises an outer body. The outer body is an exterior aspect of the device and is meant to be held by the user. The outer body may comprise one or more layers, these one or more layers formed uniformly or disparately of one or more materials. In this manner, the material for the outermost layer of the outer body may be selected for its aesthetic value, comprising qualities of a desirable look and/or feel, while one or more inner layers of the outer body may be selected for functionally relevant qualities, such as heat and/or electrical conductivity, durability, and cost. Alternatively, the outer body may comprise a single layer of a material selected on account of the overall acceptability of aesthetic and functional qualities. Examples of materials include anodized aluminum, steel, ceramic, polycarbonate plastic, and magnesium.

In one embodiment, the outer body comprises a non-smooth region, featuring raised and unraised areas. The non-smooth region is designed to be held by the user such that the raised areas are in direct contact with the user's skin whereas the unraised areas are not in direct contact but, as it were, separated by air packets. In this manner, the user can maintain a firm grip on the device while only touching a minimal area. On account of this minimal contact, less heat will be conveyed from the device to the user's skin and the use of the device will be consequently more comfortable and enjoyable.

In one embodiment, the outer body may be designed so that one or more interior aspects can be accessed or controlled by the user. Accordingly, the outer body may comprise one or more recesses; these one or more recesses allow buttons, indicators, or other interactive components to protrude or be sufficiently exposed for user interaction. The one or more recesses may be actual through gaps in the outer body, so that, if isolated from the rest of the device, the one or more recesses would provide an at least partially visible gap in the material.

In one embodiment, the outer body may comprise one or more concave areas. These concave areas facilitate intentional interaction between the user and the one or more buttons in the concave areas, while impeding accidental engagement. For example, if the device is placed in a pocket or purse, next to an object such as a wallet, the object will be unlikely to press against or engage the one or more buttons. The width of the concave area is such that objects of a smaller radial area, such as a finger or a pen, will be able to easily engage while objects of a larger radial area will not because they will be blocked by the shallow ends of the concave region. The one or more concave areas may span an entire dimension of the outer body, or may be limited along a given dimension.

In one embodiment, the device comprises an inner body. The inner body is disposed within the outer body, and is a positive spatial area containing negative spatial areas, and shaped so that components of the device, described below, may be supportedly disposed within the inner body. The inner body may comprise one or more layers, such that each layer is made of a material selected because of its one or more useful qualities. For example, one layer of the inner body may be made of material selected for its heat transfer capacity, thereby drawing off the heat from other components, while another layer may be made of material selected for its relative lack of heat transfer capacity, or insulating quality, so that heat does not travel through the positive spatial area from one component to another, or from one or more components to the outer body. Examples of materials include glass lined plastic, polycarbonate, ultem, and aluminum. The outer body and inner body may maintain their connectiveness or substantially flush contact by any suitable means, such as a tight fit, screws, magnetic coupling, snap fit mechanisms, all of which will be described in relation to other components, below.

In one embodiment, the device comprises a bottom lid. In one embodiment, the bottom lid comprises a lip that at least partially surrounds the surface where the bottom lid approaches the outer body. This lip is configured such that a user may be able to press against it using his or her thumb with enough force sufficient to overcome the attachment means, so that the bottom lid can be at least partially removed from the outer body.

In one embodiment, the bottom lid is attached or attachable to the outer body and/or inner body by magnetic coupling. In this embodiment, one or more magnets disposed on or in the bottom lid engage with one or more magnets disposed on or in the outer body and/or the inner body. In another embodiment, the bottom lid is attached or attachable to the outer body and/or the inner body by a tight fit, which is accomplished by maintaining at least one dimension of the bottom lid the same or substantially the same as at least one dimension of the outer body and/or the inner body. This tight fit may be increased by tapering an orthogonal aspect of one or more of the at least one dimensions. In yet another embodiment, the bottom lid is attached or attachable to the outer body and/or the inner body by the engagement of male and female threads, disposed either respectively or in the reverse. In yet another embodiment, the bottom lid is attached though not spatially fixed to the outer body and/or the inner body by means of one or more hinges, so that the bottom lid and the outer body and/or the inner body are rotationally although incompletely separable. In yet another embodiment, the bottom lid is attached or attachable to the outer body and/or the inner body by the engagement of tongue and mouth mechanisms, such that the user created force necessary for the tongue to click into position inside the mouth is less than the force necessary to unclick and thereby unengage the bottom lid from the outer body and/or the inner body is less in magnitude or different in kind. The difference in magnitude or kind is a result of the gradual versus sudden deformation of the material—a sudden deformation of material requires a burst of force or a change in force, whereas a gradual deformation of material requires a maintenance of force across an interval.

In another embodiment, the inner body may comprise one or more heat sinks. These heat sinks may trap heat based on the insulating material that comprises the heat sink. They may be disposed adjacent to heating elements, chambers, and/or between the inner body and the outer body. The heat sinks may also be disposed adjacent to the concentrate and/or herbal channels, thereby helping to cool down the air transferred through the channels.

In one embodiment, the device comprises a mouthpiece. The mouthpiece is another exterior aspect of the device, and provides the user oral access to one or more interior aspects of the device. This oral access involves the use of a mouthpiece hole, through which one or more vapors, aerosols, or fluid material may flow. Such flow occurs by virtue of the user placing his or her mouth on the mouthpiece around the mouthpiece hole, and "pulling", "sucking", or otherwise "inhaling" the contents of the flow so that it passes from the interior of the device into the user's mouth and, presumably eventually, into the lungs. This result is the primary purpose of the device disclosed herein.

The mouthpiece may be made of any suitable material. The material is to be selected based on having one or more desirable qualities, such as being heat resistant or insulating, germ-resistant, and/or durable. Examples of material include heat-resistant plastic, glass-lined plastic, hard rubber, glass, ceramic, and teflon, aluminum, and steel.

In one embodiment, the mouthpiece comprises a protruding area and a base. The protruding area is connected to the base, and of a contour suitable to be pressed against and/or between the user's lips. Accordingly, the protruding area is narrower at the end than where it connects to the base. The protruding area may either be fixedly attached to or attachable to, or formed as one piece with the base. The mouthpiece hole is disposed at the end of the protruding area furthest from the base. The mouthpiece may be attached or attachable to the outer body at the base by any of the means provided in the discussion above relating to the attachment between the outer body and/or inner body and the bottom lid.

In one embodiment, the mouthpiece comprises one or more air inlets, which permit air flow from the ambient to the interior of the mouthpiece. An air inlet may function as the mere mouth of an air inlet channel, which provides a controlled flow to a specific area, thereby affecting air flow dynamics in the interior of the device in an intentional manner, or it may provide a general entry without being connected to or part of a specific air inlet channel. The flow in the air inlets is expected to be the reverse of the flow in the mouthpiece hole—the former travels inward to outward whereas the latter travels in the reverse.

The one or more air inlets may be disposed on the base and/or protruding area. Alternatively, they may be disposed in an area where the base of the mouthpiece is incompletely flush with the outer and/or inner body. In another embodiment, the air inlets are disposed elsewhere on the device, such as entirely on the outer body; accordingly, they may be directed to any interior part of the device.

In one embodiment, the mouthpiece comprises a hollow. The hollow is a negative region in the protruding area and/or the base that permits the access and mixing of one or more flows through and from various channels, inlets, and/or holes. For example, if a user inhales on the mouthpiece hole, creating a negative pressure on several air inlets and/or channels, flow will be drawn from those several air inlets and/or channels into the hollow, whereupon they will substantially mix. Thereafter, this mixed air mass will be inhaled via the mouthpiece hole. The mouthpiece hollow can also be considered a chamber. In one variation, the chamber is not in the mouthpiece but rather in the inner body. In yet another variation, the chamber is removably enclosed in the device, and may be attached to the mouthpiece, so that the mouthpiece and chamber can be removed from the device in order to be conveniently used for inhaling the mixed vapors.

In one embodiment, the protruding area of the mouthpiece comprises more than one hole, enabling the simultaneous use of the device by more than one person. In another embodiment, the protruding area comprises one or more prongs spaced apart from one another, and the holes are disposed on these separate prongs. In another embodiment, part of the protruding area of the mouthpiece is removable and replaceable.

In one embodiment, the mouthpiece comprises one or more flexible hoses, with the holes disposes on the ends of these one or more hoses.

The device may comprise at least two heating systems. Each of the heating systems may be thermally, mechanically, electrically, and spatially isolated from one another. In one embodiment, the device comprises a concentrate system. The concentrate system is a set of one or more components enabling the at least partial vaporization of physiologically relevant material that has been previously manipulated so as to increase the physiological effect. Additionally relevant are materials that contribute taste to the use of the device, even if they do not otherwise contribute physiologically. This material, in a post-concentrated, pre-vaporized state, will be referred to hereon as "concentrate", and may comprise though not be limited to one or more extracts, dehydrates, or purified forms of natural or synthetic substances. It must also be understood that the purpose of the concentrate system will still in part be achieved if non-concentrate—that is, non-manipulated matter—is used in place of or in addition to the concentrate. The concentrate may also comprise aerogel or other gas-infused materials. After vaporization, material will separate into a concentrate vapor stream and concentrate debris.

In one embodiment, the concentrate system comprises a concentrate chamber. The concentrate chamber is a storage area for the concentrate, and may be made of any suitable material. It may comprise one or more layers, such that multiple materials may be selected in order to optimize the qualitative values of each material. For example, the chamber may comprise an inner layer made of highly thermally conductive material, in order to receive heat from a heat creating means, and transfer that heat to concentrate material in contact with said inner layer; further, the chamber may comprise an outer layer made of thermally non-conductive material, in order to prevent the heat from escaping the chamber and leaking out into potentially thermally sensitive components elsewhere in the device.

In one embodiment, the concentrate chamber comprises an illumination source, such as may be provided by LEDs.

In one embodiment, the concentrate chamber is either sealed, or inlets/gaps are fitted with semi-porous screens that limit through-transport to vaporized particles and keeps out liquids, etc.

In one embodiment, the concentrate system comprises one or more concentrate heating elements. The one or more concentrate heating elements may be disposed within, without, or in between layers of the heating chamber. The one or more concentrate heating elements may be made of any suitable material, provided that they can transform electrical energy into heat. This transformation may be achieved by a concentrate heating element as a whole, or by a component thereof. The concentrate heating element should be capable of heating the concentrate chamber up to 420 degrees Fahrenheit.

In one embodiment, a concentrate heating element has a concave, dish-like aspect configured to hold or support concentrate. In this embodiment, concentrate is in contact with the concentrate heating element so that the concentrate is heated directly by the concentrate heating element. In this manner, vaporization occurs by conduction. In another embodiment, the concentrate is held or supported by a support structure located adjacent to the concentrate heating element, so that there is some space between one or more parts of the support structure for air to flow; the concentrate heating element heats the air flow, which, as it moves about the concentrate, heats the concentrate; in this manner, vaporization occurs by convection.

In one embodiment, an air flow region at least partially separates the concentrate chamber from the concentrate heating element. This separation should be such that air flow, which may consist of a smaller volume, is possible, while transport of solid particulates is not possible or at least impeded. This air flow is a part of the flow from the reverse concentrate channel, described below. After passing through the air flow region, the air flow "picks up" or "joins" the vapor from the convection/conduction process described above, and at that point becomes the concentrate vapor stream. Thereafter, it flows through the concentrate channel, described below.

In one embodiment, the concentrate system comprises a debris well. The debris well sits adjacent to, though not entirely in contact with, the concentrate heating element, and on an opposite side from which the concentrate is held or supported by the heating element. The debris well is designed to divert and catch any solid particulate that passes through the air flow region. The diversion of particulate flow into the well may be accomplished by one or more walls attached to or formed together with the debris well and positioned so that air flow is possible past an unattached end of the wall while particulate is less likely to pass by that unattached end because it would require that the particulate follow a path that winds in mutually distinct directions.

In one embodiment, the concentrate system comprises a concentrate channel. The concentrate channel provides a flow path by which the concentrate vapor created in the concentrate chamber reaches, at least eventually, the mouthpiece hole. Accordingly, the concentrate channel is disposed at one end of the concentrate chamber, possibly on the same side of a concentrate heating element as the concentrate itself. Between the concentrate chamber and the mouthpiece hole, the concentrate channel may split into one or more sub-channels, and/or it may join one or more channels of the same or different compositions.

In one embodiment, the concentrate system comprises one or more reverse concentrate channels. The reverse concentrate channels provide a flow path by which air enters the concentrate chamber; after at least partially mixing with the vapors resulting from the vaporization occurring in the chamber, the said air effectively becomes the concentrate vapor. Thereafter, it enters the concentrate chamber, as described above.

In one embodiment, the concentrate channel is disposed at least in part within the reverse concentrate channel. In this embodiment, the concentrate channel opens into one end of the concentrate chamber, and the reverse concentrate channel opens into the other end; however, the concentrate chamber is also disposed within the reverse concentrate channel. In another embodiment, the reverse concentrate channel is disposed at least in part within the concentrate channel. In this embodiment, the reverse concentrate channel opens into one end of the concentrate chamber, and the herbal channel opens into the other end; however, the concentrate chamber is also disposed within the concentrate channel. In either of these embodiments, the direction of flow in the concentrate channel is generally opposite that of the reverse concentrate channel, except where the outer channel that contains the inner channel and the chamber opens into the chamber, whereupon the flow direction of in the outer channel in part reverses.

In one embodiment, the device comprises one or more channel guides. A channel guide comprises a stopper and a channel embedded in the stopper. The stopper at least partially covers and/or enters one side of a chamber, thereby limiting direct fluid flow from the chamber except through the channel embedded in the stopper. This construction puts the fluid flow in closer contact with the channel walls, facilitating greater heat transfer from the flow to the channel.

The one or more channel guides may act as concentrate and/or herbal channel guides, in that they principally engage with one or more concentrate and/or herbal chambers and are embedded with one or more concentrate and/or herbal channels. The one or more channel guides may be attached, attachable to, or formed as one piece with the mouthpiece.

In one embodiment, the device comprises an herbal system. The herbal system is a set of one or more components enabling the at least partial vaporization of physiologically relevant material that, unlike the concentrate system, has not been previously manipulated. Additionally relevant are materials that contribute taste to the use of the device, even if they do not otherwise contribute physiologically. This material, in a pre-vaporized state, will be referred to hereon as "herbal", and may comprise, for example, plant parts such as leaves, stems, bark, roots, etc. After vaporization, material will separate into an herbal vapor stream and herbal debris. It must also be understood that the purpose of the herbal system will still in part be achieved if concentrate, as described above, is used in place of or in addition to the herbal material.

In one embodiment, the herbal system comprises an herbal chamber. The herbal chamber is a storage area for herbal matter, and may be made of any suitable material. It may be comprise one or more layers, such that multiple materials may be selected in order to optimize the qualitative values of each material. For example, the chamber may comprise an inner layer made of highly thermally conductive material, in order to receive heat from a heat creating means, and transfer that heat to herbal material in contact with said inner layer; further, the chamber may comprise an outer layer made of thermally non-conductive material, in order to prevent the heat from escaping the chamber and leaking out into potentially thermally sensitive components elsewhere in the device.

In one embodiment, the herbal system comprises an herbal heating element. The herbal heating element may comprise a thin film heater. It may be disposed within the herbal chamber, either in the walls themselves, or in the cavity region, and may be made of either a polyamide or ceramic material. Alternatively and/or additionally, the herbal heating element may be disposed outside the herbal chamber. The herbal heating element may provide heat to the chamber sufficient to heat it to 440 degrees Fahrenheit. In yet another alternative, the herbal heating element may comprise a ceramic heater with kanthal or nichrome resistive wires baked into the structure.

In one embodiment, the herbal system comprises an herbal channel. The herbal channel provides a flow path by which the herbal vapor created in the herbal chamber reaches, at least eventually, the mouthpiece hole. Accordingly, the herbal channel is disposed at one end of the herbal chamber, possibly on the same side of an herbal heating element as the herbal material itself. Between the herbal chamber and the mouthpiece hole, the herbal channel may split into one or more sub-channels, and/or it may join one or more channels of the same or different compositions. The herbal channel may be made of steel, ceramic, or glass.

In one embodiment, the herbal system comprises one or more reverse herbal channels. The reverse herbal channels provide a flow path by which air enters the herbal chamber; after at least partially mixing with the vapors resulting from the vaporization occurring in the chamber, the said air effectively becomes the herbal vapor. Thereafter, it enters the herbal chamber, as described above.

In one embodiment, the herbal channel is disposed at least in part within the reverse herbal channel. In this embodiment, the herbal channel opens into one end of the herbal chamber, and the reverse herbal channel opens into the other end; however, the herbal chamber is also disposed within the reverse herbal channel. In another embodiment, the reverse herbal channel is disposed at least in part within the herbal channel. In this embodiment, the reverse herbal channel opens into one end of the herbal chamber, and the herbal channel opens into the other end; however, the herbal chamber is also disposed within the herbal channel. In either of these embodiments, the direction of flow in the herbal channel is generally opposite that of the reverse herbal channel, except where the outer channel that contains the inner channel and the chamber opens into the chamber, whereupon the flow direction of in the outer channel in part reverses.

In one embodiment, the herbal channel is cospacious with the herbal chamber—that is, the herbal chamber and herbal channel are not distinct parts but instead express different functions of a single structure.

The herbal and concentrate channels may be made of any suitable material or combination of materials. The choice of material may be based on the expected and/or desired temperature of the flow passing through or around that channel. For example, if the desired temperature of a flow is cool, while the expected temperature of that flow is hot, the material selected will be one that transfers heat easily, so that heat may in part leave the flow and enter the channel.

Additional features of the channels include one or more sets of braces, which help maintain an acceptable range of vibration. The braces may exist in the form of tongs or protrusions that fill in the negative space between one channel and what that channel should be spatially maintained against. Alternatively or in the addition, o-rings may serve a similar purpose, with the added ability of controlling the passage of particulate or vapor. Regardless of the kind of brace, it may be made of any suitable material, especially silicon, polycarbonate, and other heat resistant, flexible materials. Holes may be formed in the set of one or more braces so that material of a certain size—namely, vapor—may pass through, while material of a larger size—namely, particulate—may not.

In one embodiment, the concentrate and/or herbal system comprises one or more cartridges. The one or more cartridges may comprise any or all of the components of the concentrate and/or herbal system as described, and may contain or receive any relevant pre-vaporized matter. A temporary security lock or skirt may seal a concentrate cartridge on one or more sides, and may be removably attachable via a click-in-place mechanism, such as a button, or may be unattachable once removed, such as by a weakened or thinned line portion of the material by which the security lock or skirt is torn off.

The one or more cartridges may lock into place by any suitable attachment means in the inner and/or outer body. The outer body may comprise a recess through which the one or more cartridges are inserted. The outer body may comprise a hinged or sliding door, so as to seal a concentrate cartridge within the device, or a concentrate cartridge may comprise an exterior portion that is visibly disposed on the outside of the device. The hinged or sliding door, or the exterior portion of a concentrate cartridge may be modeled so as provide a continuity with the outer body, or may, at least in part, be differentiated so as to indicate to the user that therein lies the concentrate cartridge.

In one embodiment, a concentrate cartridge comprises an access area that enables a user, via a pull-tab or sliding means, to open a concentrate cartridge so as to refill the contents. In another embodiment, a concentrate cartridge is sealed by the manufacturer so as to prevent a user of the device from opening it. In one embodiment, a concentrate cartridge comprises a single-action gate and the device comprises a penetration means. The single-action gate can only or best be opened by the penetration means of the device, or is designed in some manner as to impede or limit its opening by the user. Once the single-action gate is opened, it cannot or at least with difficulty be closed again. For example, the single-action gate may comprise a narrow area of material, smaller in at least one dimension, than the radius of a finger-tip. In this example, the penetration means comprises a thin, oblong point or projection that is able to push forward, slide away, or puncture the narrow area of material. Alternatively or additionally, the single-action gate may comprise a rotatable area of material, with or without a keyhole crevice, and the penetration means comprises a key-type end. In this latter embodiment, the penetration means mechanically, with or without the assistance of the user, enters and rotates the rotatable area of material so as to permit an opening into the cartridge.

In one embodiment, the concentrate and/or herbal systems comprise one or more infrared heaters. These one or more infrared heaters may be disposed within or without the one or more chambers. An infrared heater may comprise metal wire elements, heat lamps, or any other suitable type. In another embodiment, the heating element may be modular, enabling the replacement of an old, burnt-out, or otherwise undesirable heating element with another. The modularity may extend beyond the actual heating element to components of the device that connect directly or lie adjacent to the heating element, such as one or more channels, wires, chambers, structural components, and/or any other feature mentioned or reasonably implied, suggested, or inspired by this disclosure. For example, components necessary for conductive heating may be replaced by ones that enable convective heating. In one embodiment, the heating element may comprise a thermistor.

In one embodiment, device comprise one or more screens, or filters. These filters may comprise one or more openings, these openings configures so that vapor but not solid matter may escape pass through. In one embodiment, one or more filters may be placed at least in part within a channel. In another embodiment, one or more filters may be placed within a chamber and adjacent or near an opening of the chamber.

In one embodiment, the one or more chambers and relevant systems are disposed in the device so as to provide the user access to them in order to replenish the chambers with their requisite material. For example, the herbal chamber may be disposed near or adjacent to the bottom lid. The bottom lid may comprise a stopper to close off one end of the herbal chamber; when the bottom lid and stopper are removed, the user can deposit herbal material therein. As another example, the concentrate chamber may be disposed near or adjacent to the mouthpiece. The mouthpiece may comprise a stopper to close off one end of the concentrate chamber; when the mouthpiece and stopper are removed, the user can deposit concentrate therein. In other embodiments, the chambers may be placed elsewhere, such as adjacent to or near an otherwise nondescript aspect of the outer body and within a cavity or partial cavity of the inner body. The near or adjacent part of the outer body may comprise a removable panel, that removable panel itself comprising a stopper, that stopper closing off one end of a chamber. When the panel and stopper are removed, the user may deposit the relevant material in the chamber therein.

In one embodiment, the one or more chambers are removable. In this embodiment, a chamber may be placed within a negative space of the inner body shaped to fit. There may be protrusions which a user may grab with his or her fingers or by aid of a tool in order to extract the chamber from the inner body. The chambers may be made of material which is easy to clean, such as borosilicate glass or high density ceramic. Also, the chambers may have enclosed heaters connecting to metal pins or ports accessible on the exterior of the chamber, thereby allowing a chamber to be replaced with another chamber.

In one embodiment, the device comprises a circuit board. The circuit board receives input from the one or more buttons or controls The user, through the interface of the controls, may independently control each of the one or more heaters. The user may also control one or more heaters heaters simultaneously according to the algorithms stored and executed via the circuit board's computer readable memory. The circuit board controls the flow of electricity from one or more power supplies and directs it to the one or more heaters.

In one embodiment, the set of one or more buttons include a three stage switch. Of the three stages, one corresponds to the activation of the concentrate system, one corresponds to the activation of the herbal system, and one corresponds to the activation of both systems simultaneously. In this aspect of this embodiment, the set of one or more buttons also may include an on/off button or switch, so that in the off position, there is now electricity flow and consequently neither of the systems is activated, while in the on position, electricity flow occurs so as to enable one of the three stages.

In another embodiment, one stage corresponds to the activation of the concentrate system, one corresponds to the simultaneous activation of the concentrate system and the herbal system, and one corresponds to an "off" position, in which neither systems are activated. In this embodiment, the set of one or more buttons may also include an "herbal" button or switch, so that when the three stage switch is in the stage that corresponds to the activation of the concentrate system, turning on the herbal button or switch triggers an activation of the herbal system; this activation is maintained while the herbal button is held, or in the case of a switch, that switch is in a herbal position.

In yet another embodiment, one corresponds to the activation of the herbal system, one corresponds to the simultaneous activation of the concentrate system and the herbal system, and one corresponds to an "off" position. In this embodiment, the set of one or more buttons may also include a "concentrate" button or switch, so that when the three stage switch is in the stage that corresponds to the activation of the herbal system, turning on the concentrate button or switch triggers an activation of the concentrate system; this activation is maintained while the concentrate button is held, or in the case of a switch, that switch is in a concentrate position.

In one embodiment, the device comprises one or more indicator lights. These one or more indicator lights may be of and light-emitting kind, such as an light emitting diode or LED. The set of one or more indicators may indicate, based on the on/off status of the light, the color of the light, or Morse-like pattern of on/off status and/or color, whether the herbal and/or concentrate system is activated, the herbal and/or concentrate heating element is sufficiently hot for vaporization to occur, and whether the one or more batteries powering the herbal and/or concentrate heating element is low on charge and must be replaced/recharged.

The one or more batteries may be rechargeable, and may comprise one or more single cell rechargeable batteries and/or 18650/18350 batteries. The batteries may be disposed in a battery module removably disposed in the inner body. The battery module may be externally and/or internally embedded with electrical pins or wire ends, permitting the batteries as power supplied to be instantly connected to the circuit board when the battery module is replaced in the inner body.

In one embodiment, the device comprises a timer connected to the circuit board or microprocessor. The timer can be initiated after electricity is sent to the one or more heaters, or at some other significant step in the process of using the device. After the timer has run a pre-determined period of time, the device will initiate a power-off move.

In another embodiment, an accelerometer may be placed in the device. The accelerometer may be used in conjunction with the timer. When a predetermined position is recognized by the accelerometer, and a predetermined period of time has transpired as determined by the timer, the device may initiate the power-off move. These steps ensure that battery power is not wasted when the device is not in use.

In one embodiment, the device comprises a charging port. The charging port is a recess in the outer body providing access to any suitable means of receiving electric power, such as a usb port, mini-usb port, or ac adapter port. Additionally or in the alternative, the charging port may be based on electro magnetic resonance, thereby permitting the wireless charging of the device. Fli charging technology is also contemplated. In another embodiment, the device comprises a single or multiple unit battery well. The battery well may be electrically connected to the charging port so as to enable the charging of batteries therein. In one embodiment, the charging port may electrically connect to a charging dock. The charging dock is structurally able to support the device, and may provide a plug for connecting to an outlet, or may be equipped with a long-life or chargeable battery.

In one embodiment, the device comprises a power port. The power port may comprise a wire or cable for directly plugging into a wall outlet, or may comprise a connection means for said wire or cable.

In one embodiment, the device comprises a vibrating motor. Through a combination of wavelength, frequency, magnitude, and the in-sequence manipulation thereof, the vibrations that emanate from the vibrating motor may convey some or all of the same messages to the user discussed in the section on the LED indicators. In another embodiment, the vibrating motor may be used in conjunction with the LED indicators to enable the communication of more nuanced messages to the user.

In one embodiment, the device comprises a cleaning kit. The cleaning kit may comprise a housing, and one or more tools that assist in cleaning the device may be stored within the housing. This cleaning kit may be separable in whole or in part from the device. In one embodiment, the cleaning kit hooks onto the device via mating components, such as male and female threads, hook and loop fasteners, click on mechanisms, or any suitable means. In another embodiment, the cleaning kit may be fixedly attached to the device.

In one embodiment, the tools of the cleaning kit may comprise one or more wires with abrasive points, edges, or bristles, one or more brushes, and/or one or more hard scraping devices.

In one embodiment, the device may comprise air flow sensors, which may be disposed anywhere within the device, to detect the drawing of air toward the hole in the mouthpiece. This information may be communicated electronically to a microprocessor, triggering one or more actions, or may result in a direct flow of current to one or more components thereby activating them. For example, the flow of air may signal the activation of one or more heaters.

In one embodiment, the device may comprise a battery life indicator. This indicator may alert the user when battery life has dropped below a certain level, or may alert the user as the battery life drops below one or more levels. These may indication(s) may be achieved by illumination sources and/or the vibrating motor. Different illumination patterns and/or vibration pulses may indicate different characteristics of the battery life. For example, the vibrator may pulse one sequence when battery life is reduced to 50%, and another sequence when battery life is reduced to 10%.

In one embodiment, the bottom lid of the herbal chamber comprises a pressure plate and an outer layer. The outer layer is exposed to the outside of the device, while the pressure plate is designed to be in contact with the herbal material placed in the herbal chamber. In one variation, one or more springs or tension-bearing materials are placed between the pressure plate and the outer layer, thereby exerting a force tending to the separation or distancing of the pressure plate and the outer layer. When the outer layer is attached rigidly to the device, the pressure plate will move inward into the herbal chamber until it encounters a material resistance provided by the material in the chamber. The material will consequently be compressed. The more the material is compressed, the more thorough the vaporization of material. In another variation, the pressure plate is made of thermal conductive material, and will therefore apply heat to the surface of the herbal material inside the herbal chamber. In yet another embodiment, the pressure plate is electrically and/or thermally connected to the thin film heater embedded in the chamber, thereby providing for uniform heating throughout the herbal chamber. The more uniform the application of heat, the more thorough the vaporization.

In one embodiment, the device comprises a haptic feedback vibrating motor or similar electrically induced vibration producing component. Current will be sent to the vibrating motor, causing it to vibrate, upon one or more of the following conditions: a stage has been selected by the user, a heating element has heated to a designated maximum temperature, a chamber has used-up a designated amount of material, a chamber has only a designated amount of material left, the device has been turned on, or the device has been turned off. In addition to or instead of a vibration, the device may emit an illumination pattern using one or more illumination sources.

The device may be structured in several different orientations. Generally, the device is cylindrical or pinched-cylindrical (have one two sides an angle rather than a curve). In one orientation, the mouthpiece is disposed on the top, the concentrate chamber is disposed on the top beneath the mouthpiece, and the herbal chamber is disposed on the bottom. In one variation, the concentrate chamber and the herbal chamber are each disposed on the sides, either left or right.

In one embodiment, the the controls may be embedded or adorned with capacitive touch sensors to determine whether a person's fingers are being used to turn on the device, or some other object is unintentionally rubbing against or contacting the controls. This ensures that only intentional activation occurs. In a variation, the capacitive touch sensors can receive one or more sets of fingerprints, the circuit board and concomitant algorithms can digitize the fingerprints, and deny permission to activate the device unless one of the one or more sets of fingerprints are used to engage the controls.

In one embodiment, air flow sensors situated in the mouthpiece, one or more channels, or one or more chambers, can detect the volumetric flow or related characteristics of the user's intake. This parameter can be compared to pre-determined parameter or range of parameters through the device's circuit board processing, and communicate to the user by illumination means, vibrating means, or a display, whether the user is sucking in too much or too little air. The communication can be in the form of a game, where one set of graphical user interface objects representing the user's intake is aligned or unaligned with another set of graphical user interface objects representing an ideal intake. For example, two co-centric circles and/or crosshairs may serve as the GUI objects.

In one embodiment, the device comprises a heated apex that protrudes from the concentrate chamber module toward the mouthpiece tower. The apex may be somewhat cylindrical or conical, and longer than it is wide. The apex may engage with a downward facing pick, which may be used to deposit concentrate on or in the dish, or merely provide a component that can be used to add concentrate generally to the chamber. The pick is also somewhat cylindrical or conical, and longer than it is wide. It may be attached to a substantially disc-shaped component whose periphery is substantially flush against the inner walls of the chamber. The dish-pick is removably disposed in the concentrate chamber and graspable by a human hand. The pick would be attached to the bottom portion of the disc, oriented toward the bottom of the chamber. The top portion of the disc may comprise a tab to be grasped by the user. The disc prevents splash or leakage from entering the concentrate channel while permitting vaporized material to pass through. This may be because of the material comprising the disc, which may be a kind of grating.

DETAILED DESCRIPTION

Figure 1:
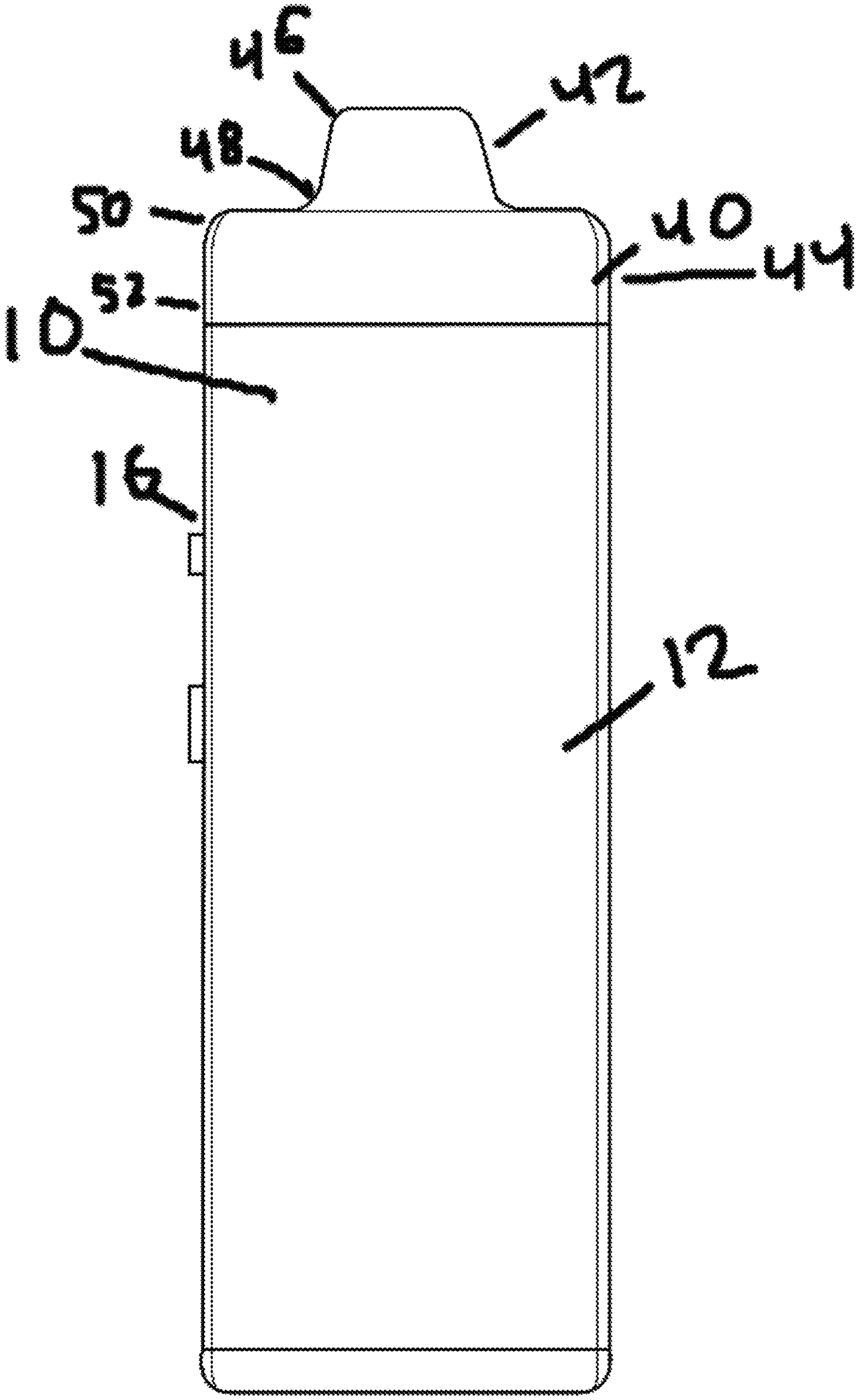
FIG. 1 shows an exterior view of an exemplary device.
Figure 2:
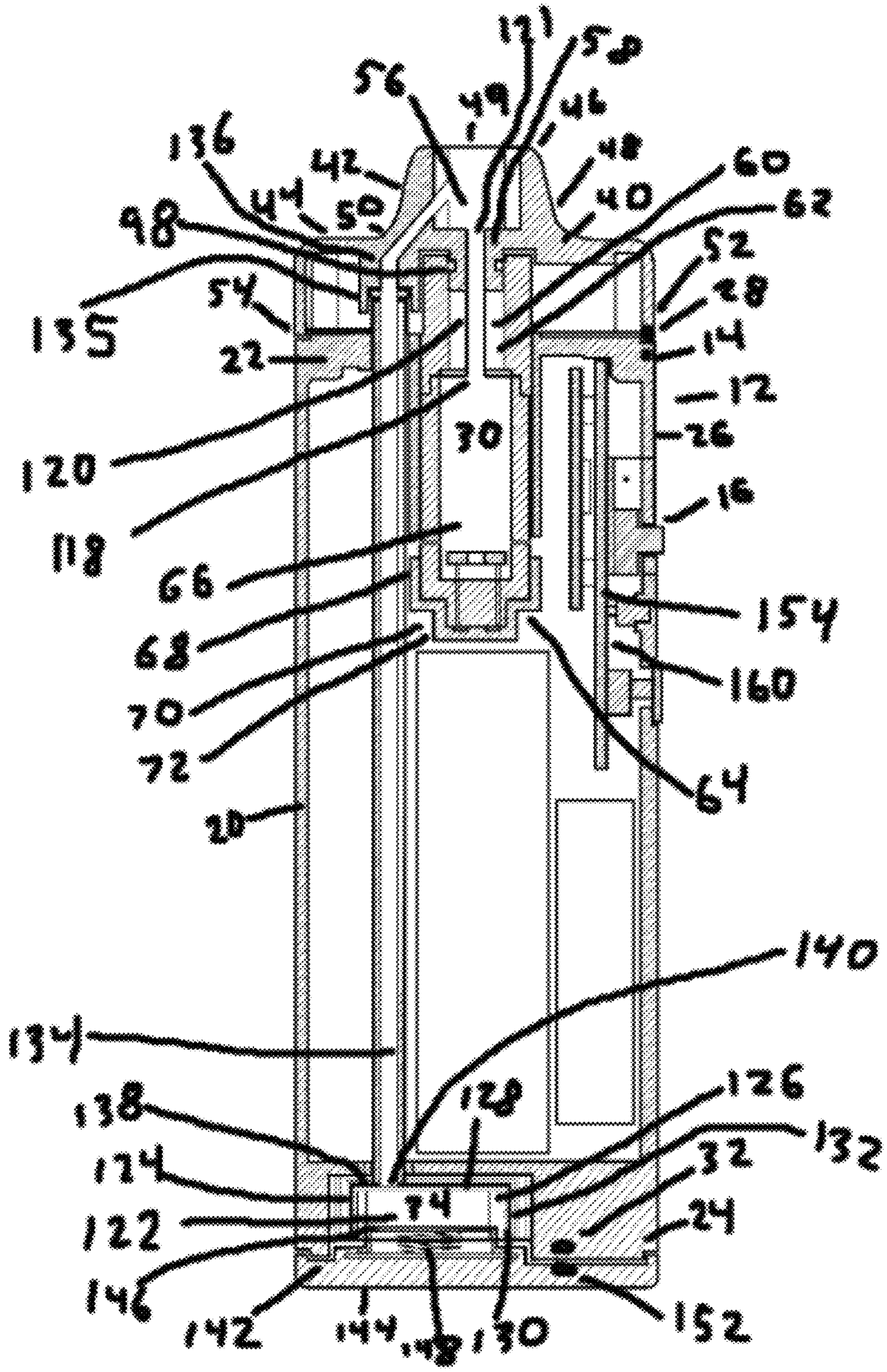
FIG. 2 shows an interior view of an exemplary device.
Figure 3:
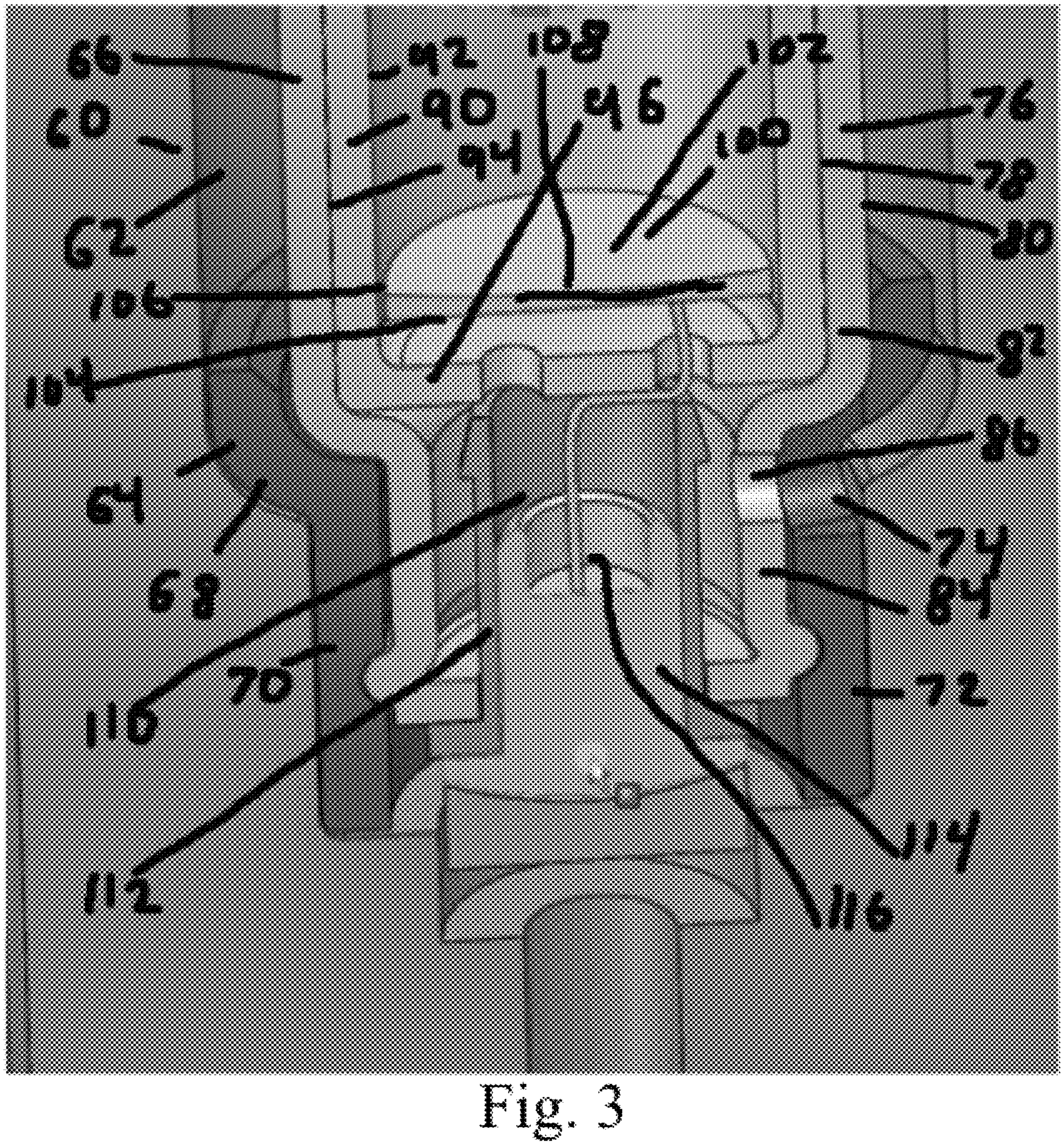
FIG. 3 shows an interior view of an exemplary device.
Figure 4:
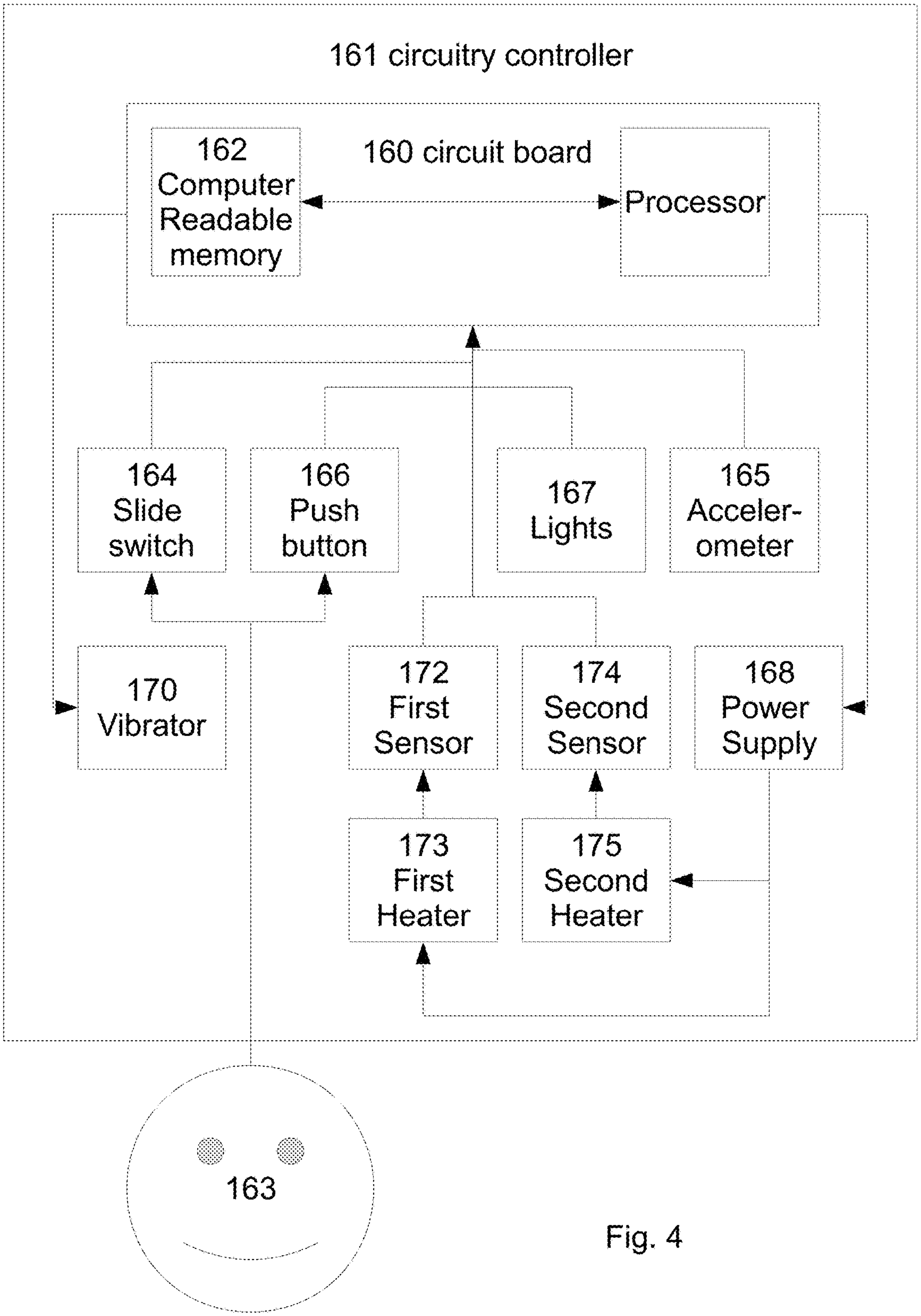
FIG. 4 shows a flowchart of an exemplary device.
Figure 5:
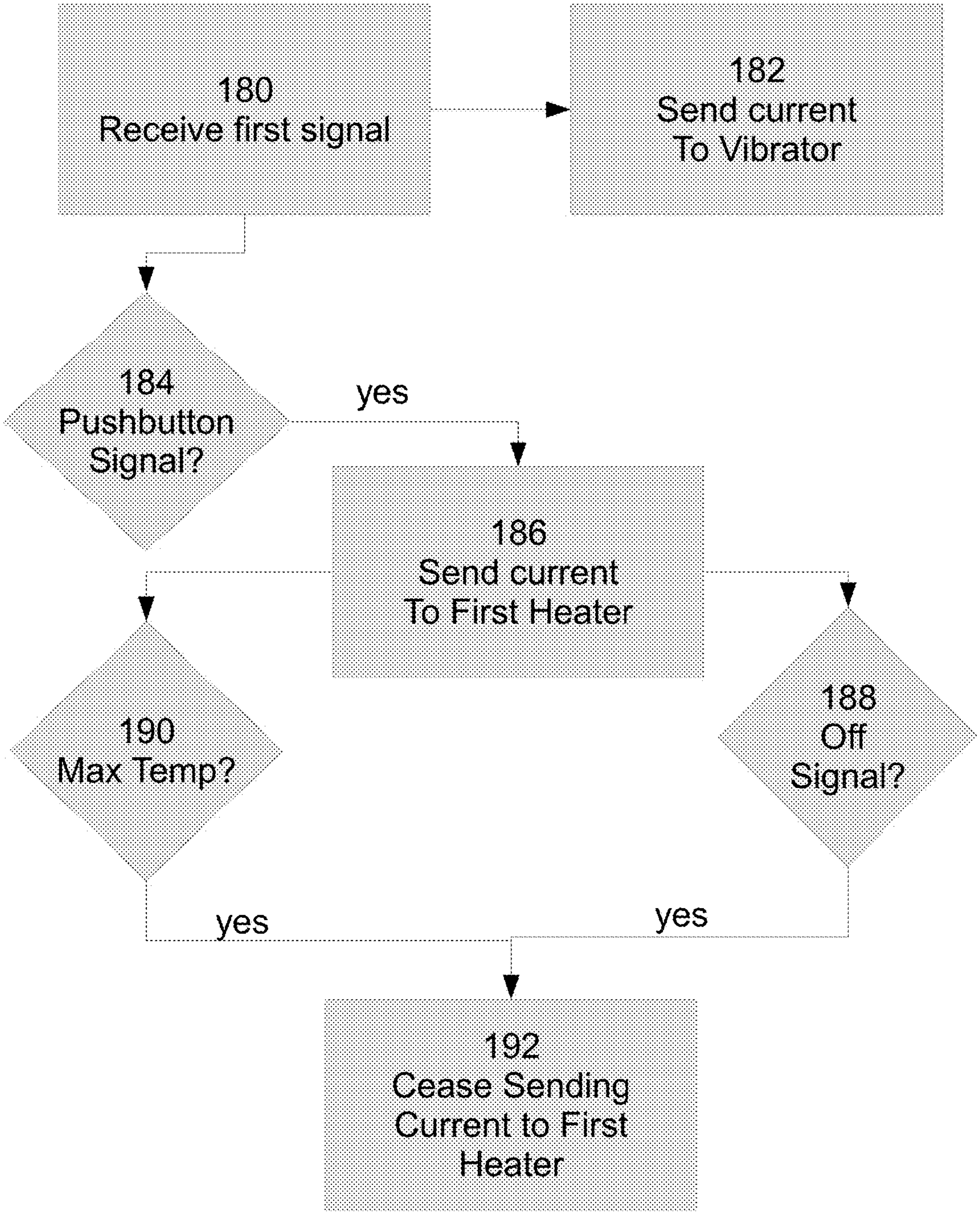
FIG. 5 shows a flowchart of an exemplary program run by a device.
Figure 6:
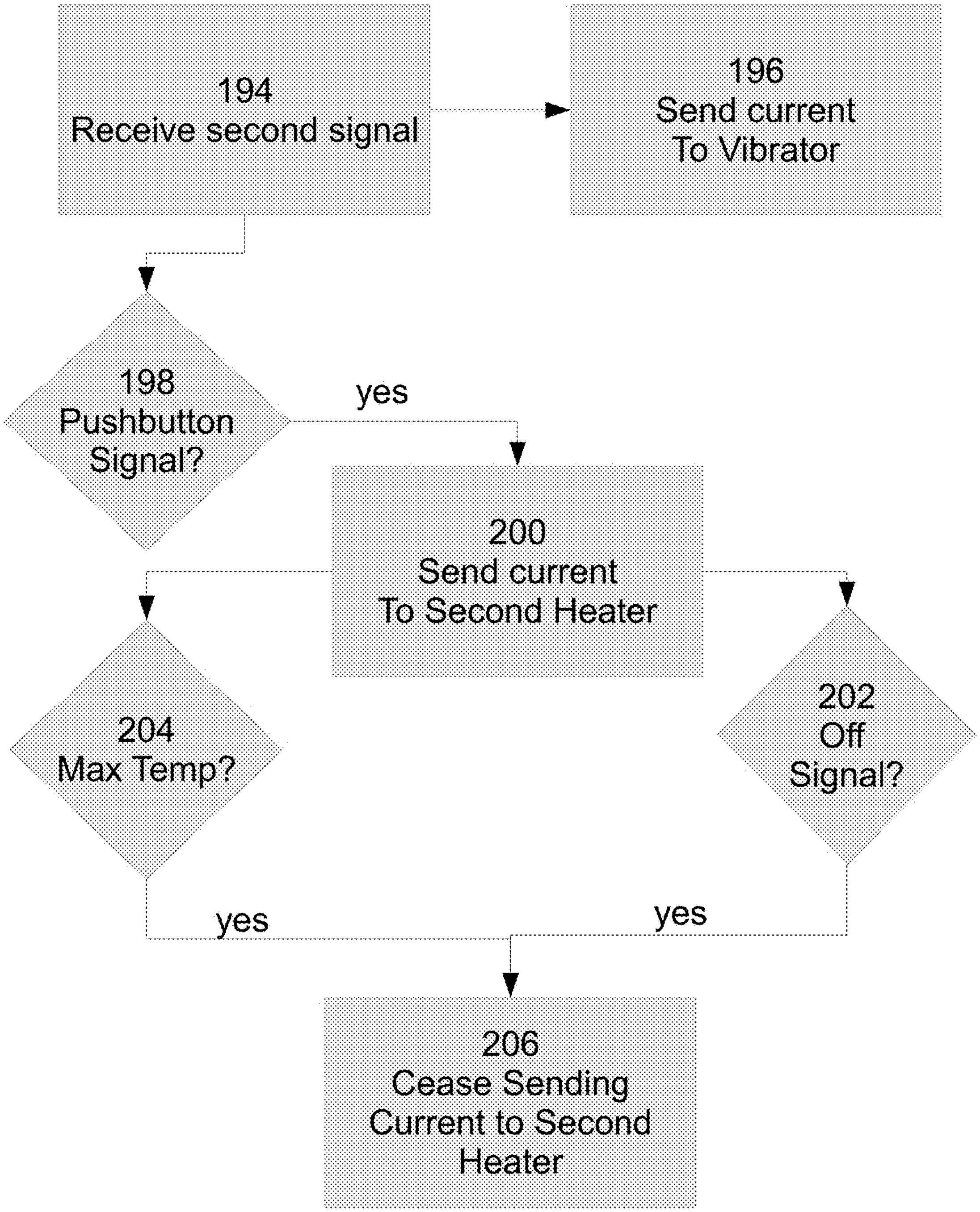
FIG. 6 shows a flowchart of an exemplary program run by a device.
Figure 7:
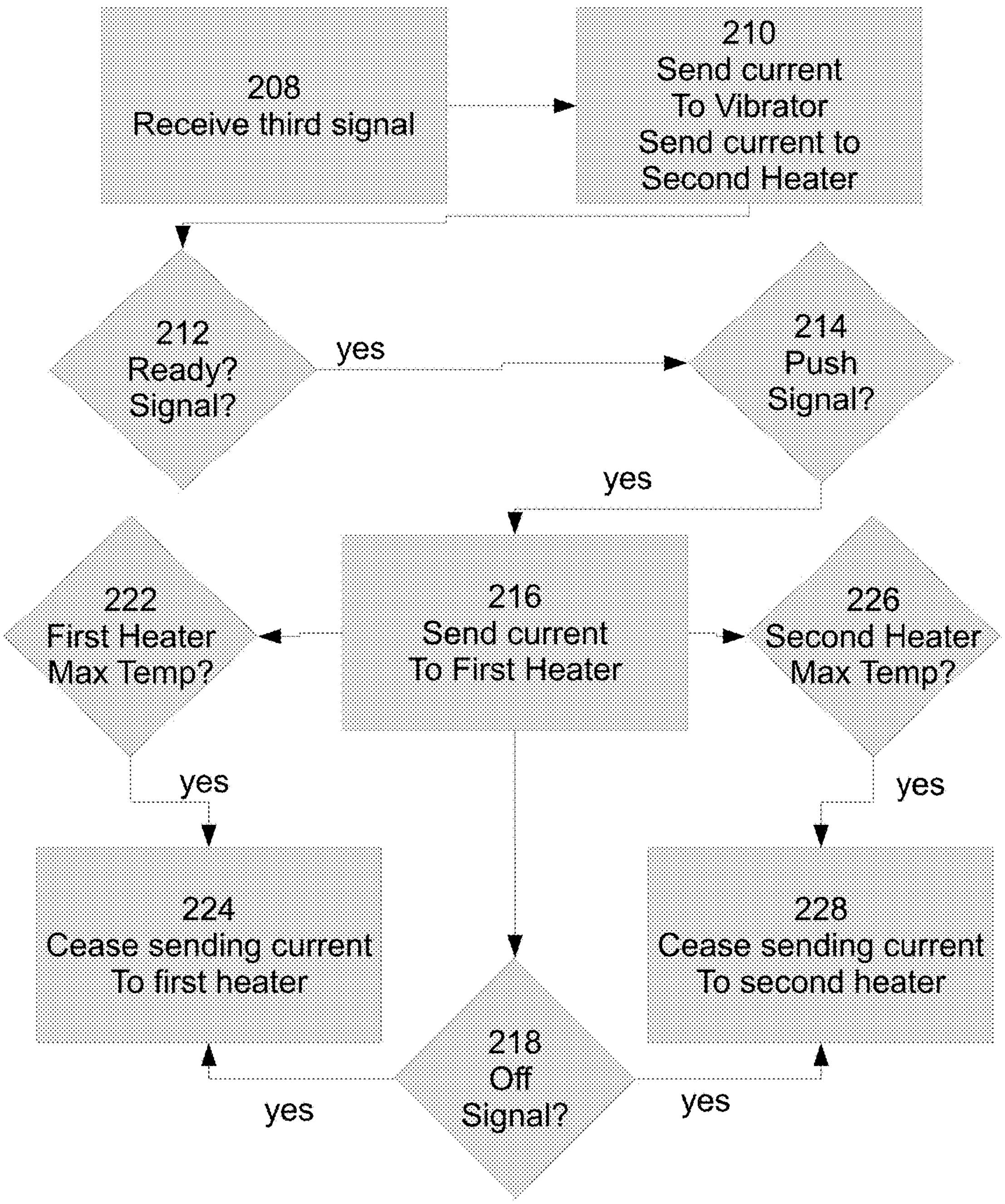
FIG. 7 shows a flowchart of an exemplary program run by a device.

In the embodiment shown in FIG. 1, the device comprises an outer housing 10. The outer housing may be made of anodized aluminum, steel, ceramic, polycarbonate plastic, or magnesium. The outer housing is exposed to the atmosphere, and therefore must be durable. The outer housing may have an outer surface 12, and inner surface 14, and one or more gaps 16.

In another embodiment, the device may comprise an inner housing 20. The inner housing may be made of glass, plastic, or glass-lined plastic. The thermal conductivity of the inner housing is ideally less than 0.3 W/mK. It may have a proximal end 22, and a distal end 24, and an outer surface 26. The proximal end may be embedded with one or more proximal end magnets 28, and a concentrate chamber recess 30. The distal end may be embedded with one or more distal end magnets 32, and an herbal chamber recess 34. As can be seen, the outer surface is flush against the inner surface of the outer housing. The recesses are negative space areas in the inner housing.

In another embodiment, the device may comprise a mouthpiece, 40. The mouthpiece may be made of polycarbonate, hard rubber, glass, ceramic, and teflon, aluminum, and steel. It may have a protruding portion 42, and a base 44. The protruding portion may be shaped into a narrow end 46, a wider end 48, and a mouthpiece hole 4. The mouthpiece hole may be disposed on the narrow end. The base may be connected to the wide end of the protruding portion at an upper portion 50. A lower of the base may be embedded with base magnets 52. These base magnets may engage with the proximal magnets of the inner body, so that the mouthpiece may be removably attached to the bulk of the device.

At least one set of prongs 54 may protrude from the lower portion of the base. The prongs provide a guide through which air may flow into the device. They are disposed adjacent to gaps in the outer housing. The air flow provided by these prong-guided gaps mixes with air and/or vapor in a mouthpiece chamber 56. The mouthpiece chamber is in fluid communication with the mouthpiece hole discussed above, as well as many other air filled chambers and channels. The mouthpiece chamber is in part bordered by a mouthpiece tower 58, which protrudes from the lower portion of the base. The mouthpiece tower is shaped so that it does not obstruct air flow from the prong-guided gaps into the mouthpiece tower.

The device further comprises a concentrate system 60, which primarily occupies the concentrate chamber recess. The concentrate chamber recess acts in part as a reverse concentrate channel 62, which permits air from the prong-guided gaps may flow into the reverse concentrate channel. Within the reverse concentrate channel is a cradle 64, and a concentrate chamber 66, which is secured by the cradle. The cradle may be made of silicone, polycarbonate, and has an upper portion 68 and a lower portion 70. The lower portion may be narrower than the upper portion, enabling a more secure fit for the concentrate chamber. Also, the lower portion has a vertically inclined or diagonal wall 72 with a hole 74 disposed in it, permitting air flow from the reverse concentrate channel into the cradle. The cradle may be embedded with magnets that engage with magnets embedded in the concentrate chamber, thereby increasing the sureness of the fit.

The concentrate chamber may have more than one layer, including a shell 76 made of stainless, aluminum, ceramic, glass, or plastic. The shell has an inner wall 78, an outer wall 80, an upper portion 82, and a lower portion 84. A hole 86 may be disposed in the lower portion. This same hole may align with the hole in the cradle, enabling air to continue flowing from the cradle into the shell. The lower portion of the shell is also surrounded by the lower portion of the cradle, and preferably in flush contact with it.

The device may also comprise an enclosure 90 designed as an inner housing for the concentrate chamber. This enclosure may be housed in the upper portion of the shell to be, among other things, closer to the mouthpiece and therefore more readily receive concentrated material. The enclosure may be made of ceramic. By making the enclosure out of ceramic, the chamber will maintain less heat after the heat supply is removed, and thereby prevent over baking of the concentrate received therein. The enclosure may be designed to receive at least 15 mL of material.

The enclosure may feature an inner wall 92, an outer wall 94, and a floor 96. The outer wall may be flush with the inner wall of the shell, thereby preserving a heat seal. The inner wall and outer wall may be two sides of the same wall. The inner wall may wrap around the enclosure and be substantially sealed on the bottom by the floor. However, the floor may feature at least one hole 98 in order to provide for fluid communication with the reverse concentrate channel.

An o-ring 98, perhaps of silicone, may be fitted between the mouthpiece tower, which may protrude into the concentrate chamber, and the enclosure. The o-ring provides for a tight seal to prevent air in the concentrate chamber from directly mixing with air in the reverse concentrate channel.

A receptacle for receiving the concentrate material, such as a dish 100, may be disposed in the upper portion of the chamber. A top surface 102 of the dish may be facing the mouthpiece tower, and a bottom surface 104 may be facing the enclosure floor. The top surface is ideally a concave contour in order to best receive the concentrate. The dish may be bordered by a periphery 106. This periphery, which may or may not have walls that prevent concentrate material from spilling over onto the floor, may be fixed to the inner wall of the enclosure or the the floor of the enclosure. But a part of the periphery must not touch the inner wall of the enclosure in order to permit some fluid communication between the enclosure and the lower portion of the shell. The dish may be made of ceramic and with a first heater or concentrate heating element 108 baked into it. The heating element should be capable of being heated to at least 380 F.

A debris well 110 may be situated in the lower portion of the shell. It is designed to catch any debris that falls through the air gaps between the periphery of the dish and the inner wall and down into the hole in the floor. The debris well comprises a wall 112 that surrounds it on all sides. This top edge of this wall may be incompletely flush with the floor of the enclosure in order to permit some air flow between the enclosure and the lower portion of the shell.

The debris wall may house an atomizer 114. This atomizer, which converts electrical energy into heat, may be connected to the ceramic heater by a thermally conductive connection, such as a metal wire 116 or filament. The metal wire may pass through the floor hole in connecting to the heater in the dish. Once the atomizer sends the heat to the heater, the concentrate on the dish may vaporize. The vapor may travel out of the enclosure through a first opening 118 of a concentrate channel 120 disposed in the mouthpiece tower, through a second opening 121 into the mouthpiece chamber. The concentrate chamber connects to the enclosure on the side of the enclosure opposite the atomizer.

The device may also be fitted with a herbal chamber 122, which may be disposed in the herbal chamber recess of the inner housing. In one embodiment, the herbal chamber is not fixedly attached to the herbal chamber recess but instead can be removed by a user by pulling on a tab of some sort attached to the herbal chamber.

The herbal chamber may have a shell 124 which provides a structural support for an enclosure 126. The enclosure may be made of glass, ceramic, steel, or aluminum, and may be disposed in the shell. It should comprise an upper portion 128 and a lower portion 130, the upper portion being flush against the herbal chamber recess. Embedded in the shell, the enclosure, or between them is a second heater of some sort, perhaps a polyamide thin film heater 132. The second heater may be designed to be capable of heating up to a temperature of 440 F, and up to 360 F in less than 60 seconds. The heater and enclosure may have at least 2.5 square inches of contact together to ensure proper heating of the contents of the enclosure. The enclosure may also be designed to receive up to 45 mL of herbal material.

An herbal channel 134 may also be disposed in a recess of the inner housing. The herbal channel may be made of glass and held in place within the inner housing by one or more braces 135 such as an o-ring. The o-ring may be made of silicone or some other appropriate material that substantially prevents, limits, or amends vibrations. There may be some space between the outside of the herbal channel and the inner housing in order to prevent the herbal channel and the inner housing from touching. The herbal chamber may have a first opening 136 connected to the mouthpiece chamber and a second opening 138 connected to the upper portion of the herbal chamber.

The device may comprise a heat insulating in an air chamber surrounding the herbal chamber. The air chamber walls may be made of thermally non-conductive material.

Between the herbal channel and the herbal chamber there may be a disc 140, or filter comprising one or more holes. The disc may be made of stainless steel, aluminum, or ceramic. The one or more holes should be large enough to provide for fluid communication between the herbal chamber and the herbal channel, but not large enough for macro particles or the like to float up the channel. The diameter of a given hole is ideally between 0.02 and 0.045 inches.

The herbal chamber may be on one or more sides detachably sealed by a bottom lid 142. The bottom lid has an outer portion 144, which may be made of plastic, an inner portion 146, which may be made of a material with a thermal conductivity of at least 50.2 W/mK, and may have a spring 148 or other pressure-exerting component disposed between the inner portion and the outer portion. When the bottom lid is closed against the herbal chamber, the spring will exert a force against the inner portion which would then exert a force against the herbal material placed therein. This helps pack more herbal material into the chamber. Also, since the inner portion is capable of communicating heat against the herbal material, it ensures a greater surface area of vaporization, and therefore a more thorough and uniform vaporization.

In order to provide a superior seal as well as an area that the user can use to pry the bottom lid from the device, the bottom lid may comprise a lip 150 that protrudes slightly from the the outer housing, thereby providing a surface area that a finger or thumb can engage with. The bottom lid may also be embedded with one or more magnets 152 that engage with the one or more distal end magnets.

It should be noted that the mouthpiece tower at least partially protrudes into the concentrate chamber and the reverse concentrate channel is in fluid communication with the ceramic dish through the hole in the silicone cradle, the hole in the shell, the hole in the floor of the enclosure, and the portion of the ceramic dish not connected to the inner wall of the enclosure.

In one embodiment, the device has an accelerometer 154 to help determine the orientation of the device.

In one embodiment, the device is fitted with a circuitry controller 161 for enabling the user to selectively heat the two chambers. The circuitry controller comprises a circuit board 160, which provides the functionality of any microprocessor or computer. The circuit board is provided a computer-readable storage memory 162, connections to input devices including a slide switch 164 or first controller, a pushbutton 166 or second controller, at least one power supply 168, a haptic feedback vibrating motor 170, a ceramic heater temperature sensor 172 or first heater temperature sensor, and a thin film heater temperature sensor 174 or second heater temperature sensor. Thermistors may be used in place of the one or more heater temperature sensors. It is also conceivable that a more reduced or simplified version of the circuit board can be implement, one in which one or more of the above components are combined or missing. The circuit board may also be connected to the accelerometer 165 and one or more illumination sources 167. The power supply is connected to a first heater, such as the ceramic heater 173, and the second heater, such as the thin film heater 175. The first heater temperature sensor is connected to the first heater and the second heater temperature sensor is connected to the second heater. The user 163 may operate on the slide switch and push button.

The circuit board may be programmed to 180 upon receiving a first stage signal from the slide switch, 182 send current to the vibrating motor. If no other stage signal is received, and 184 a pushbutton signal or on signal from a pushbutton or second controller is received, the circuit board may 186 send current to the first heater, which may be a ceramic heater, or the atomizer that is connected to the ceramic heater. If 188 the push signal is no longer received, or an off signal is received, or 190 a maximum temperature signal is received from the ceramic heater temperature sensor, then 192 the circuit will cease sending current to the ceramic heater.

The circuit board may be programmed to 194 upon receiving a second stage signal from the slide switch, 196 send current to the vibrating motor. If no other stage signal is received, and 198 a pushbutton signal is received, the circuit board may 200 send current to the thin film heater. If 202 the push signal is no longer received, or 204 a maximum temperature signal is received from the thin film heater temperature sensor, then 206 the circuit will cease sending current to the ceramic heater.

The circuit board may be programmed to 208 upon receiving a third stage signal from the slide switch, 210 send current to the vibrating motor and send current to the thin film heater until 212 a ready temperature signal is received from the thin film heater temperature sensor. If 214 a pushbutton signal is received, 216 send current to the ceramic heater. If 218 the pushbutton signal is no longer received, 224 cease sending current to the ceramic heater and 228 cease sending current to the thin film heater. If 222 the maximum temperature signal is received from the thin film heater temperature sensor, 224 cease sending current to the thin film heater. If 226 the maximum temperature signal is received from the ceramic heater temperature sensor, 228 cease sending current to the ceramic heater.

The invention claimed is:

1. A device for generating vaporized material comprising:

an outer housing comprising an inner surface, an outer surface, and one or more gaps;

an inner housing made material with a thermal conductivity of less than 0.3 W/mK and comprising:

a proximal end embedded with one or more magnets and comprising a concentrate chamber recess;

a distal end embedded with one or more magnets and comprising an herbal chamber recess; and an outer surface that is flush against the inner surface of the outer housing;

a mouthpiece, comprising:

a protruding portion comprising a narrow end, a wider end, and a mouthpiece hole disposed on the narrow end;

a base comprising an upper portion that is connected to the wider end of the protruding portion and a lower portion that is embedded with magnets that engage with the magnets embedded in the proximal end of the inner housing;

at least one set of prongs that protrude from the lower portion of the base and are disposed adjacently to at least one of the one or more gaps in the outer housing;

a mouthpiece chamber in fluid communication with the mouthpiece hole and in fluid communication with at least one of the one or more gaps through the at least one set of prongs; and a mouthpiece tower that is attached to the lower portion of the base;

a reverse concentrate channel disposed within the concentrate chamber recess;

a cradle disposed within the reverse concentrate channel and comprising an upper portion and a lower portion, the lower portion comprising a wall, the wall comprising a hole;

a concentrate chamber disposed in the cradle, comprising:

a shell comprising an inner wall, an outer wall, an upper portion, and a lower portion, where the lower portion comprising a hole, the hole aligns with the hole in the cradle, and the lower portion is surrounded by the cradle;

a ceramic enclosure capable of receiving at least 15 mL of material, disposed in the upper portion of the shell, and comprising an inner wall, an outer wall, and a floor, where the outer wall of the enclosure is flush against the inner wall of the shell and the floor comprises at least one hole in fluid communication with the reverse concentrate channel;

an o-ring disposed and fitted between the mouthpiece tower and the enclosure;

a ceramic dish for receiving concentrate material and comprising a bottom surface, a top surface, and a periphery, where the top surface features a concave contour and at least a portion of the periphery is not attached to the inner wall of the enclosure;

a concentrate heating element baked into the ceramic dish and capable of being heated to at least 380 F;

a debris well disposed in the lower portion of the shell and comprising a wall, where the wall is incompletely flush with the floor of the enclosure; and an atomizer disposed within the debris well and connected to the concentrate heating element by a metal connection, where the metal connection passes through the hole in the floor of the enclosure;

a concentrate channel disposed in the mouthpiece tower and comprising a first opening and a second opening, where the first opening is connected to the mouthpiece chamber and the second opening is connected to the enclosure on a side of the enclosure opposite the atomizer;

an herbal chamber removably disposed in the herbal chamber recess of the inner housing and comprising a shell comprising:

a thin film heater able to heat up to a temperature of 440 F and capable of heating up to 360 F in less than 60 seconds;

an enclosure disposed within the shell, capable of receiving 45 mL of material, and having at least 2.5 square inches of contact area with the heater;

a lower portion; and an upper portion, where the upper portion is flush against the herbal chamber recess;

an herbal channel held in place within the inner housing by one or more o-rings and comprising a first opening and a second opening, where the first opening is connected to the mouthpiece chamber and the second opening is connected to the upper portion of the herbal chamber;

a disc disposed between the herbal channel and the herbal chamber and comprising at least one hole that provides for fluid communication between the herbal chamber and the herbal channel, the at least one hole measuring between 0.02 and 0.045 inches in diameter;

a bottom lid, comprising:

an outer portion, an inner portion made of material with a thermal conductivity of at least 50.2 W/mK, a spring disposed between the outer portion and the inner portion, a lip that at least partially protrudes from the outer housing, and one or more magnets that engage with the one or more magnets in the distal end of the inner housing;

an accelerometer to determine orientation; and a circuitry controller comprising:

a circuit board disposed in the inner body, having a computer-readable storage memory, and connected to a slide switch, a pushbutton, at least one power supply, a haptic feedback vibrating motor, a ceramic heater temperature sensor, and a thin film heater temperature sensor, the circuit board programmed to:

upon receiving a first stage signal from the slide switch, send current from the power supply to the vibrating motor, and then, upon receiving a push signal from the pushbutton, send current from the power supply to the ceramic heater, but if the push signal from the pushbutton is no longer received, or a maximum temperature signal is received from the ceramic heater temperature sensor, cease sending current from the power supply to the ceramic heater;

upon receiving a second stage signal from the slide switch, send current from the power supply to the vibrating motor and send current from the power supply to the thin film heater until a ready temperature signal is received from the thin film heater temperature sensor, and then, upon receiving a push signal from the pushbutton, continue sending current from the power supply to the thin film heater, but if the push signal from the pushbutton is no longer received, or a maximum temperature signal is received from the thin film heater temperature sensor, cease sending current from the power supply to the thin film heater; and upon receiving a third stage signal from the slide switch, send current from the power supply to the vibrating motor and send current to the thin film heater until a ready temperature signal is received from the thin film heater temperature sensor, and then, upon receiving a push signal from the pushbutton, continue sending current from the power supply to the thin film heater and begin sending current from the power supply to the ceramic heater, but:

if the push signal from the pushbutton is no longer received, cease sending current to the ceramic heater and cease sending current to the thin film heater;

if the maximum temperature signal is received from the thin film heater temperature sensor, cease sending current to the thin film heater; and if the maximum temperature signal is received from the ceramic heater temperature sensor, cease sending current to the ceramic heater;

where: the mouthpiece tower at least partially protrudes into the concentrate chamber and the reverse concentrate channel is in fluid communication with the ceramic dish through the hole in the cradle, the hole in the shell, the hole in the floor of the enclosure, and a space the ceramic dish and the inner wall of the enclosure.

2. A device for generating vaporized material comprising:

an outer housing;

an inner housing made of different material from the outer housing and comprising an outer surface that is flush against the outer housing;

a mouthpiece comprising a mouthpiece hole and a mouthpiece chamber, where the mouthpiece hole is in fluid communication with the mouthpiece chamber;

a reverse concentrate channel disposed in the inner housing and in fluid communication with the mouthpiece chamber;

a concentrate chamber disposed within the reverse channel, comprising:

an enclosure comprising an upper portion and a lower portion;

a dish for receiving concentrate material, disposed in the upper portion of the enclosure and comprising a first heating element;

an atomizer disposed in the lower portion of the enclosure and connected to the first heating element; and a concentrate channel connecting the mouthpiece chamber to the upper portion of the enclosure, where the concentrate channel is not in direct fluid communication with the reverse concentrate channel except through the mouthpiece chamber on one end and the lower portion of the enclosure on another end;

an herbal chamber comprising an enclosure, where the enclosure comprises a second heater and is disposed within the inner housing;

an herbal channel disposed within the inner housing and in direct fluid communication with the enclosure of the herbal chamber and the mouthpiece chamber; and a bottom lid attached to the herbal chamber.

3. The device in claim 2, where the mouthpiece further comprises a protruding portion and a base, where the protruding portion comprises a narrow end and a wider end, with the mouthpiece hole disposed on the narrow end, the wider end connected to the base, and the base connected to the outer housing.

4. The device in claim 3, where the base further comprises a hole that is in fluid communication with the mouthpiece chamber but is not identical to the mouthpiece hole.

5. The device in claim 3, where the enclosure further comprises a floor separating the upper portion and the lower portion, where the floor comprises at least one floor hole that occupies less than 30% of the surface area of the floor, an enclosure hole is disposed in the lower portion of the enclosure, and a debris well is disposed in the lower portion of the enclosure; and where the first heater is a ceramic heater, the second heater is a thin film heater, the upper portion of the enclosure is in fluid communication with the lower portion of the enclosure through the at least one floor hole, the lower portion of the enclosure is in fluid communication with the reverse concentrate channel through the enclosure hole, and the atomizer is disposed within the debris well and connected to the heating element by a metal connection passing through the floor hole of the enclosure.

6. The device in claim 3, where the reverse concentrate channel is disposed within a proximal end of the inner housing and the herbal chamber is disposed within a distal end of the inner housing.

7. The device in claim 6, further comprising a disc disposed between the herbal channel and the herbal chamber and comprising at least one hole.

8. The device in claim 6, with the herbal channel held in place within the inner housing by one or more braces such that a majority of an outside surface area of the herbal channel is not in direct contact with the inner housing.

9. The device in claim 6, where the bottom lid comprises an outside portion, an inner portion made of material with a thermal conductivity of at least 50.2 W/mK, and a spring disposed between the outer portion and the inner portion.

10. The device in claim 7, where the herbal chamber is removably disposed in the inner housing.

11. The device in claim 7, further comprising a metallic net removably disposed in the herbal chamber, with the metallic net being flush against one or more walls of the herbal chamber.

12. The device in claim 5, where the concentrate chamber further comprises an illumination source.

13. The device in claim 3, where the mouthpiece further comprises a mouthpiece tower, the mouthpiece tower protrudes at least 1 cm into the concentrate chamber, and the concentrate channel is embedded in the mouthpiece tower.

14. The device in claim 2, further comprising a circuitry controller comprising: a circuit board disposed in the inner body and having a computer-readable storage memory and connections to a first controller, a second controller, at least one power supply, a first heater temperature sensor, and a second heater temperature sensor, the circuit board programmed to:

upon receiving a first stage signal from the first controller and an signal from the second controller, send current from the power supply to the first heater, but if the on signal from the second controller is no longer received, or a maximum temperature signal is received from the first heater temperature sensor, cease sending current from the power supply to the first heater;

upon receiving a second stage signal from the first controller, send current from the power supply to the second heater until a ready temperature signal is received from the second heater temperature sensor, and then, upon receiving on signal from the second controller, continue sending current from the power supply to the second heater, but if the on signal from the second controller is no longer received, or a maximum temperature signal is received from the second heater temperature sensor, cease sending current from the power supply to the second heater; and upon receiving a third stage signal from the first controller, send current to the second heater until a ready temperature signal is received from the second heater temperature sensor, and then, upon receiving an on signal from the second controller, continue sending current from the power supply to the second heater and begin sending current from the power supply to the first heater, but:

if the on signal from the second controller is no longer received, cease sending current to the first heater and cease sending current to the second heater;

if the maximum temperature signal is received from the second heater temperature sensor, cease sending current to the second heater; and if the maximum temperature signal is received from the first heater temperature sensor, cease sending current to the first heater.

15. The device in claim 14, where the first heater is a ceramic heater and the second heater is a thin film heater.

16. A device for generating vaporized material comprising:

an outer housing;

an inner housing;

a mouthpiece comprising a mouthpiece hole;

a first chamber disposed within the inner housing, in fluid communication with the mouthpiece hole through a first channel, and comprising a first heating element and a first receptacle for receiving vaporizable material;

a second chamber disposed within the inner housing, in fluid communication with the mouthpiece hole through a second channel, and comprising a second heating element and a second receptacle for receiving vaporizable material; and a circuitry controller comprising: a circuit board disposed in the inner body and having a computer-readable storage memory and connections to a first controller, a second controller, at least one power supply, a first heater temperature sensor, and a second heater temperature sensor, the circuit board programmed to:

upon receiving a first stage signal from the first controller and an signal from the second controller, send current from the power supply to the first heater, but if the on signal from the second controller is no longer received, or a maximum temperature signal is received from the first heater temperature sensor, cease sending current from the power supply to the first heater;

upon receiving a second stage signal from the first controller, send current from the power supply to the second heater until a ready temperature signal is received from the second heater temperature sensor, and then, upon receiving on signal from the second controller, continue sending current from the power supply to the second heater, but if the on signal from the second controller is no longer received, or a maximum temperature signal is received from the second heater temperature sensor, cease sending current from the power supply to the second heater; and upon receiving a third stage signal from the first controller, send current to the second heater until a ready temperature signal is received from the second heater temperature sensor, and then, upon receiving an on signal from the second controller, continue sending current from the power supply to the second heater and begin sending current from the power supply to the first heater, but:

if the on signal from the second controller is no longer received, cease sending current to the first heater and cease sending current to the second heater:

if the maximum temperature signal is received from the second heater temperature sensor, cease sending current to the second heater; and if the maximum temperature signal is received from the first heater temperature sensor, cease sending current to the first heater.

17. The device in claim 16, where the mouthpiece further comprises a protruding portion and a base, where the protruding portion comprises a narrow end and a wider end, with the mouthpiece hole disposed on the narrow end, the wider end connected to the base, and the base connected to the outer housing.

18. The device in claim 17, where the base further comprises a hole that is in fluid communication with the mouthpiece chamber but is not identical to the mouthpiece hole.

19. The device in claim 18, where:

the device further comprises a reverse channel;

the first chamber further comprises an upper portion, a lower portion, a debris wall, and a floor;

the floor separates the upper portion from the lower portion and comprises at least one floor hole that accounts for less than 30% of the surface area of the floor;

the lower portion comprises a lower portion hole;

the debris well is disposed in the lower portion;

the first heater comprises a ceramic heater and an atomizer;

the second heater is a thin film heater;

the upper portion of the first chamber is in fluid communication with the lower portion of the first chamber through the at least one floor hole;

the lower portion is in fluid communication with the reverse channel through the lower portion hole; and the atomizer is connected to the ceramic heater by a metal connection passing through the at least one floor hole of the first chamber.

20. The device in claim 19, where the second chamber further comprises a bottom lid, and the bottom lid comprises an outside portion, an inner portion made of material with a thermal conductivity of at least 50.2 W/mK, and a spring disposed between the outer portion and the inner portion.

* * * * *